United States Patent [19]

Khan et al.

[11] Patent Number: 4,612,373
[45] Date of Patent: Sep. 16, 1986

[54] TRICHLORO, 6-SUBSTITUTED SUCROSE COMPOUNDS, COMPOSITIONS AND USES THEREFOR

[75] Inventors: Riaz A. Khan, Sonning; Khisar S. Mufti, Reading; Gita D. Patel, Tadley, all of England

[73] Assignee: Tate & Lyle Public Limited Co., England

[21] Appl. No.: 531,604

[22] Filed: Sep. 12, 1983

[30] Foreign Application Priority Data

Sep. 13, 1982 [GB] United Kingdom ............... 8226058
Jun. 24, 1983 [GB] United Kingdom ............... 8317238

[51] Int. Cl.⁴ .................... A61K 7/16; A23L 1/09; C07H 5/02
[52] U.S. Cl. ...................... 536/120; 424/48; 424/49; 426/3; 426/658; 514/53; 536/122
[58] Field of Search .............. 536/122, 120; 424/48, 424/49, 180; 426/658, 3; 514/53

[56] References Cited

U.S. PATENT DOCUMENTS

| | | | |
|---|---|---|---|
| 4,324,888 | 4/1982 | Rathbone | 536/122 |
| 4,335,100 | 6/1982 | Robyt et al. | 424/180 |
| 4,362,869 | 12/1982 | Jenner et al. | 536/122 |
| 4,380,476 | 4/1983 | Mufti et al. | 536/122 |
| 4,405,654 | 9/1983 | Lee | 424/180 |
| 4,435,440 | 3/1984 | Hough et al. | 424/180 |

Primary Examiner—Johnnie R. Brown
Attorney, Agent, or Firm—Ostrolenk, Faber, Gerb & Soffen

[57] ABSTRACT

Compounds of the general formula:

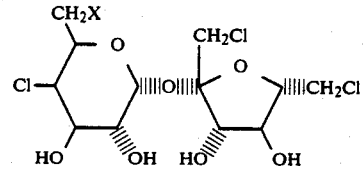

I (in which X represents a hydrogen atom or an alkoxy or arylalkoxy group) are new compounds; those where X represents a hydrogen atom or a methoxy group are potent sweeteners while those with a cleavable 6-ether group are key intermediates in the preparation of 4,1',6'-trichloro-4,1',6'-trideoxygalactosucrose (TGS). They are prepared by chlorinating a sucrose 6-ether, by etherifying a suitably protected derivative of TGS or, in the case where X represents hydrogen, by debromination of 6-bromo-4,1',6'-trichloro-4,6,1',6'-tetradeoxygalactosucrose.

9 Claims, No Drawings

TRICHLORO, 6-SUBSTITUTED SUCROSE COMPOUNDS, COMPOSITIONS AND USES THEREFOR

This invention relates to new 6-derivatives of 4,1',6'-trichloro-4,1',6'-trideoxygalactosucrose and to their use inter alia as sweeteners.

The powerful sweetener 4,1',6'-trichloro-4,1',6'-trideoxygalactosucrose, herein referred to as TGS, is described, and its use claimed, in British Pat. No. 1,543,167. It possesses a sweetening power about 600 times that of sucrose which provides a clean, pure sweetness devoid of bitterness or unpleasant after-taste. We have now discovered that a novel class of non-toxic, simple derivatives of TGS surprisingly also possess a very similar sweetening effect and/or can be used as key intermediates in the preparation of TGS.

According to the present invention we provide compounds of the general formula:

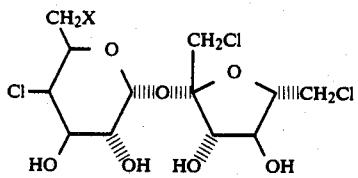

I (in which X represents a hydrogen atom or an alkoxy or arylalkoxy group).

In particular, those compounds of formula I in which X represents a hydrogen atom or a methoxy group are potent sweeteners, similar in strength to TGS itself. There is thus also provided a method of sweetening a substance comprising incorporating therein one of said sweet compounds. There is further provided an ingestible product or oral composition or a sweetening composition containing one of said sweet compounds. There is further provided a method of preparing TGS itself by reacting a compound of formula I above, in which X represents an alkoxy or aralkoxy group, with an ether-cleaving reagent.

It is surprising that the above-mentioned derivatives of TGS are very sweet, since other 6-etherified or 6-deoxy sugar derivatives have always been found to be either bitter, or at the least considerably less sweet than the parent sugar. Thus, for example, Birch and Lee (J. Food Sci. 41 (1976) 1403–1407) show that a wide range of sugar ethers are either tasteless or bitter, including various 6-etherified sucrose derivatives. However, it has now been found that a 6-ether of TGS and 6-deoxy TGS are substantially as sweet as TGS itself and are at least as stable. The new compounds according to the present invention include alkyl and aralkyl ethers. Typical alkyl ethers include lower alkyl ethers such as methyl, ethyl, isopropyl or t-butyl ethers. Typical aralkyl ethers include phenalkyl ethers such as the benzyl ether. The methyl ether especially possesses a good water solubility, taste profile and degree of sweetness (approx 500 times sucrose, compared as a 10% solution) which makes it of particular interest as an alternative to TGS. Also of particular interest is the 6-deoxy analogue (formula I, where X represents a hydrogen atom) which is approx 400 times sweeter than sucrose, compared as an 8% solution).

The sweet compounds can be formulated in any substances which are required to be sweetened.

The term "ingestible product" used herein means a product which in the ordinary course of use is intended to be swallowed, for instance a foodstuff or beverage or an orally administered pharmaceutical composition, and includes concentrates for dilution before use. The "oral composition" means a composition which in the ordinary course of use is not intended to be ingested as such, but is taken into the mouth for the treatment of throat or buccal cavity, for instance a toothpaste, toothpowder, mouthwash, gargle, troche, dental lotion or chewing gum. The term "sweetening composition" means a composition which is not itself taken orally, either to be ingested or held in the mouth, but instead is intended to be added to other ingestible products or oral compositions to render them sweet, or to increase their sweetness.

In general, the sweet derivatives according to the present invention may be used in the same manner as TGS itself. The methyl ether, for example, is approximately 500 times as sweet as sucrose (at a dilution of 10%) while the 6-deoxy analogue is approximately 400 times as sweet as sucrose (at a dilution of 8%). Thus the quantity used will, in general, be about 400 to 500 times less than the equivalent amount of sucrose needed for the required degree of sweetness. If desired, additional components can be added, e.g. components to alter the "mouthfeel" of the product.

Sweetening compositions may be formulated by mixing the sweet compound with an extender or carrier comprising any suitable vehicle for formulation into a convenient product, e.g. granules, tablets or a solution in a dropper pack. The extender or carrier may thus include, e.g. conventional water-dispersible tabletting ingredients such as starch, lactose and sucrose, e.g. spray dried maltodextrins; and aqueous solutions containing adjuvants such as stabilizing agents, colouring agents and viscosity-adjusting agents. Beverages, such as soft drinks, containing the ether derivative may be formulated either as sugar-free dietetic products, or "sugar-reduced" products containing the minimum amount of sugar required by law. The invention also comprises within its scope concentrates for dilution e.g. bottling syrups, fruit squashes, instant desserts.

The ether compounds according to the present invention may be prepared by the action of any suitable etherifying agent on TGS, which may, if required, be protected from etherification in any of the 2, 3, 3' and 4' positions. A convenient etherifying agent for the methyl ether is diazomethane, used, as is customary, in the presence of a Lewis acid such as boron trifluoride. Other etherifying agents include alkyl and aralkyl halides (for example methyl iodide used in conjunction with silver oxide—the Purdie reagent) and sulphates (for example dimethyl sulphate in an alkaline medium), and benzyl trichloroacetimidate. The 2, 3, 3' and 4'-hydroxy groups may be protected by any convenient means, such as acetalation and esterification. It is particularly convenient to form the 2,3-acetal, e.g. a 2,3-O-isopropylidene derivative, in combination with the 6-hemiacetal, and then to esterify that. Under moderate conditions (eg acetic anhydride/pyridine at room temperature) the 6-hydroxy group remains unesterified and the hemiacetal is removed during work-up. The protecting groups may then be removed after the 6-etherification.

Alternatively, the benzyl and isopropyl ethers may be obtained form the corresponding 4,6-O-benzylidene or 4,6-O-isopropylidene derivatives of sucrose esterified in the 1', 2, 3, 3', 4' and 6'-positions. These are known compounds (Khan, Carbohydrate Research 1974, 32, 375, Khan, Mufti & Jenner, ibid. 1978, 65, 109). They can be treated with mild hydride-type reducing agent, e.g. an alkali metal cyanoborohydride, to yield the corresponding 6-benzyl or 6-isopropyl ether hexa-ester which can be de-esterified to give the 6-ether of sucrose. In a manner analogous to the chlorination of a sucrose 6-ester (see British Patent Application 2,079,749A), this 6- ether can be reacted with a chlorinating agent to chlorinate the 4,1' and 6' positions selectively. A preferred chlorinating reagent, for its ease of use and its selectivity, is a reagent of the Vilsmeier type, i.e. an N,N-dialkyl(chloromethaniminium) chloride of the general formula

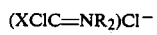

where R represents a methyl or ethyl group and X represents a hydrogen atom or methyl group.

Another chlorinating reagent which may be used is sulphuryl chloride, which reacts initially to form chlorosulphate esters of available hydroxy groups. These chlorosulphate esters are then subsequently or simultaneously decomposed with inversion of configuration, to provide the corresponding chlorodeoxy derivative. Conveniently, the chlorosulphated intermediates may be isolated, e.g. by pouring the reaction mixture into ice-cold sulphuric acid solution and extracting the acid with a solvent such as chloroform. The product obtained may be dechlorosuphated in the usual way, e.g. by treatment with a catalytic amount of an iodide such as sodium iodide, preferably in the cold. Sulphuryl chloride is, however, less selective than the Vilsmeier reagents, which are accordingly preferred.

Alternatively, the 4-hydroxy-6-ether hexa-ester obtained from the reductive cleavage of the 4,6-O-benzylidene or 4,6-O-isopropylidene derivative can be chlorinated at the free 4-position, de-esterified and then further chlorinated at the 1' and 6' positions. For this purpose, the triphenylphosphine/carbon tetrachloride reagent is very suitable.

The 6-alkyl and arylalkyl ethers of TGS can be used as key intermediates to prepare TGS itself. Reaction with an ether-cleaving reagent thus generates TGS. A particularly easy reaction involves the 6-benzyl ether, which can be hydrogenated using a catalytic system (eg Raney nickel) to remove the benzyl group and yield the 6-hydroxy product. Other ether cleaving agents include mild acid environments, e.g. a mineral acid such as hydrochloric acid, at about 1N concentration and from ambient temperature to 95° C.

6-Deoxy TGS (Formula I, X represents H) can be obtained by debromination of 6-bromo TGS, e.g. by treatment with Raney nickel in the presence of hydrazine hydrate.

The following Examples illustrate the invention further:

Example 1

6-O-Methyl TGS: 1,6-Dichloro-1,6-dideoxy-β-D-fructofuranosyl 4-chloro-4-deoxy-6-O-methyl-α-D-galactopyranose.

(a) Acetalation of TGS

A solution of TGS (18 g) in dry dimethylformamide (200 ml) was treated with 2-methoxypropene (18 ml) in the presence of p-toluenesulphonic acid (80 mg) at 70° C. for 3 h. Tlc (ethyl acetate/acetone/water 6:8:1) revealed several products and an absence of starting material. The reaction was then cooled and treated with pyridine (100 ml) and acetic anhydride 75 ml) at room temperature for 18 h. Tlc (ether-light petroleum 7:1) showed four products. The reaction mixture was concentrated to half its volume and then poured into ice/water. The precipitate was filtered off, washed with water, dissolved in ether, dried (sodium sulphate) and eluted from a column of silica gel using ether-light petroleum (1:1) to give 3',4'-di-O-acetyl-4,1',6'-trichloro-4,1',6'-trideoxy-2,3-O-isopropylidenegalactosucrose (10 g, 40% yield). The structure was confirmed by 'H-nmr and mass spectrometry.

(b) Methylation

A solution of the product of stage (a) (4 g) in dichloromethane (40 ml) was cooled to 0° C. and treated with freshly prepared diazomethane in dichloromethane (10 ml), followed by addition of a drop of boron trifluoride diethyl etherate complex, and then by further addition of diazomethane in dichloromethane (15 ml). Tlc (ethyl acetate/light petroleum 2:3) indicated formation of a single major product. The reaction was filtered and the filtrate washed with 10% sodium bicarbonate solution, and water, then dried (sodium sulphate) and concentrated to a syrup. Elution of the product from a silica gel column with ethyl acetate/light petroleum (1:3) gave 3'4'-di-O-acetyl-4,1',6'-trichloro-4,1',6'-trideoxy-2,3-O-isopropylidene-6-O-methyl-galactosucrose (3.5 g, 83%).

(c) De-Protection

A solution of the product of stage (b) (3.5 g) in acetic acid (15 ml) was treated with water (10 ml) at 70° C. for 10 min. The reaction mixture was concentrated by co-distillation with toluene and the resulting syrup taken up in methanol and treated with a catalytic amount of sodium methoxide at room temperature for 5 h. The solution was deionised by shaking with Biodeminrolit mixed bed resin ($CO_3^{2-}$-form), concentrated to a syrup and eluted from a column of silica gel using ethyl acetate-acetone (1:1) to give 6-O-methyl-TGS (1.9 g, 71%). $[\alpha]_D +76.4°$ (c 1.0, methanol).

Analysis: calc. for $C_{13}H_{21}O_8Cl_3$: C, 37.9; H, 5.10; Cl, 25.9; found: C, 39.5; H, 5.69; Cl, 22.4.

The structure of 6-O-methyl-TGS was confirmed by $^{13}C$-nmr and mass spectrometry:

'H-nmr data (200 MHz): 5.69 (d, $J_{1,2}$ 3.0 Hz, H-1), 4.12 (dd, $J_{2,3}$ 9.4 Hz, H-2), 4.24 (m, $J_{3,4}$ 1.6 Hz, H-3), 4.56 (m, H-4), 5.68 (t, $J_{3',4'}$ 6.8 Hz, H-3'), 5.44 (t, $J_{4',5}$ 6.8 Hz, H-4'), 3.40 (s, OMe), 2.09 (s, OAc), 1.42 (s, Me) 1.47 (s, Me).

$^{13}C$-n m r data: ppm 104.8 (c-2'); 94.1 (c-1); 82.6 (c-5'); 77.6 (c-3'); 77.0 (c-4'); 74.0 (c-5); 70.4 (c-6); 69.4/69.0 (c-2/c-3); 64.8 (c-4); 60.2 ($OCH_3$); 46.2 (c-1'); 45.1 (c-6').

Mass spectrum [(a) indicates hexopyranosyl cations containing 1 Cl (3:1 doublets) and (b) indicates ketofuranosyl cations containing 2 Cl (9:6:1 triplets)]: m/e 283 (b), 235 (a), 223 (b), 193 (a), 177 (a).

EXAMPLE 2

6-O-Isopropyl TGS: 1,6-Dichloro-1,6-dideoxy-β-D-fructofuranosyl 4-chloro-4-deoxy-6-O-isopropyl-α-D-galactopyranose (a) Reductive cleavage of 4,6-isopropylidene sucrose hexaacetate ring To a solution of 4,6-isopropylidene sucrose hexaacetate (5 g) in THF (50 ml) was added molecular sieve type 3A (5 g) and sodium cyanoborohydride (5 g) and then the stirred reaction mixture was cooled to 0° C.

using an ice/salt bath. The reaction mixture was acidified with HCl dissolved in ether till such a time as the effervescence ceased. Before acidification, the course of the reaction was followed on Tlc (ethyl acetate: acetone:water; 6:8:1) which indicated complete reaction in 45 minutes.

The reaction mixture was poured into methylene chloride and washed three times with a saturated solution of $NaHCO_3$, then with water; dried over $Na_2SO_4$; filter concentrated and chromatographed on a column of silica gel. Elution with ether; petrol (3:1) gave pure 4-(OH)-6-isopropyl sucrose hexaacetate (4.69; 94.5%) Nmr: shows—OH peak and fits the strucure. Reference:Garegg, Huttberg and Oscarson; J. Chem. Soc. Perkin 1,1982,2395.

Nmr ($CDCl_3$): τ4.38 (d, 1H, $J_{1,2}$ 3.5 Hz, H-1), 5.19 (q, 1H, $J_{2,3}$ 10.0 Hz, H-2), 4.61 (t, 1H, $J_{3,4}$ 9.5 Hz, H-3) 5.62 (q, 1H, $J_{4,5}$ 10 Hz, H-4), 4.54 (d, 1H, $J_{3',4'}$ 6 Hz, H-3'), 4.6 (t, 1H, $J_{4',5'}$ 6.5 Hz H-4'), 7.8–7.92 (m, 18H, $C_{12}H_{18}$), 8.8 (s, 3H, $CH_3$), 8.84 (s, 3H, $CH_3$), 8.14 (s, 1H, OH).

(b) 4-Chloro-6-O-isopropyl-galactosucrose hexaacetate:

Triphenylphosphine (6.1 g) was added to a cooled (10° C.) solution of 4-OH-6-isopropyl-sucrose hexaacetate from stage (a) (5 g) in pyridine (50 ml). After 15 minutes, carbon tetrachloride (1.6 ml) was added to the reaction mixture. The reaction mixture was taken out of the ice bath after 10 minutes, then allowed to cool to room temperature and left at this temperature for 1 hr. It was then transferred to an oil bath preheated at 80° C. for 2 hrs. Tlc (ether) showed one fast moving product. The reaction mixture was concentrated to a syrup after the addition of methanol. It was eluted from a column of silica gel using ether: petrol; 3:1) giving the title compound (4.8 g; 95%). Nmr ($CDCl_3$):τ4.26 (d, 1H, $J_{1,2}$ 3.5 Hz, H-1), 4.74 (q, 1H, $J_{2,3}$ 10 Hz, H-2), 4.64 (q, 1H, $J_{3,4}$ 3.5 Hz, H-3), 5.34 (q, 1H, $J_{4,5}$ 2 Hz, H-4), 4.5 (d, 1H, $J_{3',4'}$ 65 Hz, H-3). 4.55 (t, 1H, $J_{4',5'}$ 6.5 hz, H-4'), 7.82–7.88 (m, 18H, $C_{12}H_{18}$), 8.82 (s, 3H, $CH_3$), 8.84 (s, 3H, $CH_3$).

(c) 4-Chloro-6-O-isopropylgalactosucrose:

To a solution of 4-chloro-6-O-isopropylsucrose hexaacetate in AR methanol (30 ml), sodium methoxide (1N) was added till the pH of the solution became ca. 9. The reaction mixture was left at room temperature for several hrs. Tlc (ethyl acetate: acetone: water; 6:8:1) showed a single product. The reaction mixture was neutralised with IR 15 $H^+$-type resin and then the resin was quickly removed by filtration. It is important that the reaction mixture remains basic or just neutral because presence of acid during concentration can cleave the glycosidic linkage. The filtrate was concentrated and dried in vacuum giving the title compound (1.7 g; 97%).

(d) 6-O-Isopropyl TGS:

Triphenylphosphine (3.9 g) was added to a cooled (0° C.) solution of 4-chloro-6-O-isopropylgalactosucrose (1.5 g), in pyridine (20 ml). After about 10 minutes, carbon tetrachloride (1.3 ml) was added to the cooled solution. After about 15 minutes, the reaction mixture was taken out of the ice bath and then allowed to come to room temperature. It was left at room temperature for 1.5 hrs and then heated at 70° C. for 16 hrs. Tlc (ethyl acetate: acetone: water; 6:8:1) showed one major product moving faster than TGS and some slower and faster minor products and about 10% starting material. After the addition of methanol, the reaction mixture was concentrated to a syrup. Addition of ether crystallized most of the triphenylphosphine-based byproduct which was filtered off. The filtrate was again concentrated and eluted from a column of silica gel using ethyl acetate: acetone; 3:1 giving 6-O-isopropyl TGS (1.06 g; 65%). The product was fully acetylated (pyridine/acetic anhydride) and the nmr spectrum measured:

Nmr ($CDCl_3$):τ4.34 (d, 1H, $J_{1,2}$ 3.0 Hz, H-1). 4.7 (2H. H-2 and H-3), 5.36 (m, 1H, H-4), 4.3 (d, 1H, $J_{3',4'}$ 6.5 Hz, H-3'), 4.55 (t, 1H, $J_{4',5'}$ 6.5 Hz, H-4'), 7.84–7.9 (m, 12H, $C_8H_{12}$), 8.84 (s, 3H, $CH_3$), 8.88 (s, 3H, $CH_3$).

EXAMPLE 3

4,1',6'-Trichloro-4,6,1',6'-tetradeoxygalactosucrose (6-deoxy TGS)

(a) 6-Bromo-4,1',6'-trichloro-4,1'6'-tetradeoxygalactosucrose tetraacetate

A solution of 2,3,3',4'-tetra-O-acetyl-4,1',6'-trichloro-4,1',6'-trideoxygalactosucrose (6 g) in pyridine (60 ml) was treated with triphenylphosphine (6.12 g) and carbon tetrabromide (3.9 g) initially at 0° C. for 1 hr and then at 65° C. for 3 hrs. Tlc (ether:petrol; 4:1) showed the presence of one fast-moving product. Methanol (25 ml) was added to the reaction mixture which was then concentrated to a syrup. Elution of this syrup from a column of silica gel using ether:light petrol (2:1) gave the 6-bromo derivative which crystallized from ether/petrol.

(b) 4,1'6'-Trichloro-4,1'6,6'-tetradeoxygalactosucrose

A solution of the product from stage (a) (1 g) in methanol was refluxed with Raney nickel in the presence of barium carbonate (1 g). When refluxing started, hydrazine hydrate (1 ml) was added to the mixture. After 10 min, another 1 ml of hydrazine hydrate was added through the condenser. After 30 minutes, the reaction mixture was filtered through a filter aid and then concentrated to a syrup which, on elution from a small column of silica gel with 1% aqueous ethyl acetate, gave 6-deoxy TGS. $[\alpha]_D+87.1°$ (c 1.0, acetone); $^{13}$C-NMR spectrum ($D_2O$ solution, relative to internal DSS at 0 ppm):

| Carbon atom | chemical shift, ppm |
| --- | --- |
| 2' | 106.02 |
| 1 | 95.41 |
| 5' | 83.75 |
| 3' | 78.89 |
| 4' | 78.04 |
| 5 | 70.95 |
| 4 | 70.03 |
| 2 | 69.78 |
| 3 | 69.28 |
| 1' | 47.46 |
| 6' | 45.99 |
| 6 | 19.61 |

4,1',6'-Trichloro-4,6,1',6'-tetradeoxygalactosucrose was found to be 400 times as sweet as sucrose (8% solution).

EXAMPLE 4

6-O-Benzyl TGS: 1,6-Dichloro-1,6-deoxy-β-D-fructofuranosyl 4-chloro-4-deoxy-6-O-benzyl-α-D-galactopyranoside.

(a) 1'2,3,3',4',6'-Hexa-O-acetyl-6-O-benzyl sucrose (1).

Molecular sieve powder type 3A (10 g) was added to a solution of 4,6-benzylidene sucrose hexaacetate (10 g) in THF (100 ml). The reaction mixture was cooled to 0° C. and sodium cyanoborohydride ($NaCNBH_3$) (15 g) was added into it. After about 10 minutes, the reaction mixture was acidified with hydrogen chloride in diethyl ether until the evolution of HCl gas ceased. The reaction was followed on tlc (ether). After about 1 hr nearly 50% product was formed. At this stage more acidified ether was added and the reaction mixture was stirred for another 1 hr. Tlc indicated (1) as the major product (90%) and some slower and faster products. The reaction mixture was diluted with dichloromethane (200 ml) and water, filtered through celite. This organic layer was separated, dried over sodium sulphate, and concentrated to a syrup. The syrup was eluted from a column of silica gel with (2:1) ether:petrol giving (1) 9 g (90% yield).

(b) 6-O-Benzylsucrose (2)

Treatment of 1 (5 g) in methanol (10 ml) with a catalytic amount of sodium methoxide at room temperature for 4 hr gave, after neutralisation with Amberlyst 15 (H+) (Registered Trade Mark) and concentration, 2 (3 g, 95%).

(c) 6-O-Benzyl-4,1',6'-trichloro-4,1'6'-trideoxygalactosucrose (3)

A solution of 2 (2 g in DMF (10 ml) was treated with Vilsmeier reagent (detailed method in British Patent 2079749) (prepared from DMF and PCl$_5$), initially at 0° C. for 20 mins; and then at 120° C. for 8 hrs. The reaction mixture was cooled to 20° C. and methanolammonium hydroxide (2:1, ml) was added, the temperature being maintained below 50° C. The solution was concentrated to give, after purification on a small column of silica (using 1:1, ethyl acetate:acetone), 3 (0.67 g, 30%), mp 55°–57° C.; $[\alpha]_D + 5.8°$.

Mass spectral data: [ions marked (a) are hexopyranosyl ('galacto') cations and ions marked (b) are ketofuranosyl cations]:

M/e 271a, 199b, 180a, 163b, 144a, 127b.

EXAMPLE 5

Preparation of TGS from 6-benzyl ether (a) 6-O-Benzyl-4,1',6'-trichloro-4,1',6'-trideoxyglactosucrose tetraacetate (4)

Conventional treatment of the product of Example 4 with acetic anhydride (2 ml) and pyridine (5 ml) at room temperature for 6 hrs gave 4 (0.68 g, 100%).

(b) 4,1',6'-Trichloro-4,1',6'-trideoxyglactosucrose (5)

A sample of 4 (500 mg) was dissolved in methanol (10 ml) and Raney nickel (one medium size spatula full) was added into it. To this reaction mixture 1.5 ml hydrazine hydrate was added. The mixture then stirred at room temperature for 8 hrs. Tlc (ethyl acetate:acetone:water; 6:8:1) showed one major product and a minor faster moving product. The catalyst was filtered off, the reaction mixture was concentrated and loaded on a column of silica gel. Elution with ethyl acetate:acetone, 1:1 as solvent afforded TSG (5). (0.27 g, 65%); identical with an authentic sample.

EXAMPLE 6

6-O-Benzyl TGS by benzylation of pre-chlorinated material (a) 4,1',6'-Trichloro-4,1',6'-trideoxy-6-O-tritylgalactosucrose (6)

A solution of TGS (20 g) in pyridine (200 ml) was treated with trityl chloride (28 g) at 80° C. for 1 hr. The reaction mixture was concentrated, taken up in dichloromethane, washed sequentially with water, aqueous sodium hydrogen carbonate and water, and dried over sodium sulphate. The solution was concentrated and eluted from a column of silic gel with diethyl ether to give 6 (25 g, 77%).

Conventional acetylation of 6 (10 g) with acetic anhydride (15 ml) and pyridine (100 ml) at room temperature for 6 hrs gave the peracetylated derivative 7 (12 g 95%).

(b) 2,3,3',4'-Tetra-O-acetyl-4,1',6'-trichloro-4,1'6'-trideoxygalactosucrose (8)

A solution of 7 (11 g) in 60% aqueous acetic acid (150 ml) was heated at 90° C. for 15 min. Tlc (ether-light petrol 4:1) showed a slow moving product. The solution was concentrated and eluted through a small column of silica gel with ether-light petroleum (2:1) to give 8 (6.92 g 90%).

(c) 6-O-Benzyl-4,1',6'-trichloro-4,1',6'-trideoxygalactosucrose tetraacetate (4)

A solution of 8 (5.0 g) in dichloromethane was treated with excess of benzyl-trichloroimidate at 60° C. for 6 hrs. The reaction mixture was concentrated and eluted through a column of silica gel with ether-light petroleum (2:1) to give 4 (1.7 g 30%).

(d) Treatment of 4 in dry methanol with a catalytic amount of sodium methoxide yielded 6-O-benzyl TGS identical with the product of Example 4.

EXAMPLE 7

Preparation of TGS from 6-O-isopropyl-TGS

6-O-isopropyl TGS (1.0 g) was dissolved in 10 ml of 1N hydrochloric acid and the solution was warmed at about 50° C. on a water bath for several hours. The reaction mixture was then cooled, neutralised with sodium carbonate, and evaporated to dryness in vacuo. The residue was then chromatographed on silica gel to yield pure TGS, identical with an authentic sample.

In the following examples, the methyl ether of TGS is referred to as MTGS, and the 6-deoxy analogue as DTGS.

EXAMPLE 8

Sweetening tablets for beverages

Each tablet contains MTGS (8 mg) or DTGS (10 mg) together with a dispersible tablet base (ca 60 mg9 containing sucrose, gum arabic and magnesium stearate, and is equivalent in sweetness to about 4.5 g sucrose.

EXAMPLE 9

Bulked Sweetener

A bulked sweetener having the same sweetness as an equivalent volume of sucrose (granulated sugar) is prepared by mixing the following ingredients and spray-drying to a bulk density of 0.2 g ml$^{-1}$:

| Maltodextrin solution | 22.2 g (dry weight) |
|---|---|
| MTGS or | 2.0 g |
| DTGS | 2.5 g |

The resulting composition has a sweetening power equivalent to approximately 2 kilograms of sugar.

EXAMPLE 10

Reduced calorie cola drink containing sugar
Ingredients to prepare 100 ml bottling syrup:

| MTGS or | 80 mg |
|---|---|
| DTGS | 100 mg |
| Sugar | 60 g |
| Benzoic acid | 35 g |
| Phosphoric acid (conc.) | 1 ml |

| -continued | |
|---|---|
| Cola flavour | 1.1 ml |
| Colour | ad lib |

Make up to 100 ml with mineral water.

This syrup may then be added in 25 ml doses to 225 ml aliquots of carbonated chilled mineral water.

EXAMPLE 10

Carbonated low calorie lemonade (sugar free)
Ingredients to prepare 100 ml syrup:

| | |
|---|---|
| MTGS or | 100 mg |
| DTGS | 125 mg |
| Benzoic acid | 35 mg |
| Citric acid (dry base) | 1.67 g |
| Lemon essence | 0.8 g |

Make up to 100 ml in mineral water.

This syrup can be added in 25 ml doses to 225 ml aliquots of carbonated chilled mineral water.

EXAMPLE 12

Toothpaste

| | % by weight |
|---|---|
| Dibasic calcium phosphate | 50 |
| Glycerol | 20 |
| Sodium lauryl sulphate | 2.5 |
| Spearmint oil | 2.5 |
| Gum tragacanth | 1.0 |
| MTGS | 0.03 |
| Water | 23.97 |

The ingredients are mixed to produce a spearmint flavoured toothpaste of acceptable sweetness but free from sugar or saccharin.

EXAMPLE 13

Chewing gum

| | part by weight |
|---|---|
| Polyvinyl acetate | 20 |
| Butyl phthalybutylglycolate | 3 |
| Polyisobutylene | 3 |
| Microcrystalline wax | 3 |
| Calcium carbonate | 2 |
| Flavouring/aroma | 1 |
| MTGS or | 0.07 |

| -continued | |
|---|---|
| | part by weight |
| DTGS | 0.09 |
| Glucose | 10 |

The above chewing gum base can be cut into conventional tablets or strips.

We claim:

1. A compound of the formula:

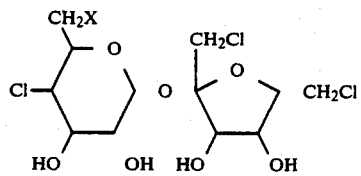

(in which X represents a hydrogen atom or a lower alkoxy or phenalkyloxy group).

2. A compound of the formula

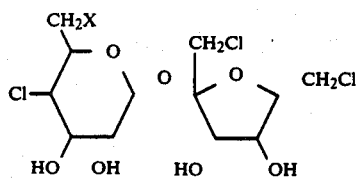

in which X represents a lower alkoxy or phenalkyloxy group.

3. A compound according to claim 2, in which X represents a methoxy group.

4. A compound according to claim 2, in which X represents a benzyloxy group or an isopropoxy group.

5. 4,1',6'-trichloro-4,6,1',6'-tetradeoxygalactosucrose according to claim 1.

6. A method of sweetening an ingestible product or oral composition by incorporating therein a sweetening amount of sweetener, wherein the sweetener is a compound according to claim 5.

7. A sweetening composition containing a sweetener mixed with an extender or carrier, wherein the sweetener is a compound according to claim 5.

8. A method of sweetening an ingestible product or oral composition by incorporating therein a sweetening amount of a sweetener, wherein the sweetener is a compound according to claim 3.

9. A sweetening composition containing a sweetener mixed with an extender or carrier, wherein the sweetener is a compound according to claim 3.

* * * * *